United States Patent [19]
Krause et al.

[11] Patent Number: 6,156,873
[45] Date of Patent: Dec. 5, 2000

[54] BISMUTH DENDRIMERS, PROCESSES FOR THEIR PREPARATION, AND THEIR USE AS X-RAY CONTRAST AGENTS

[75] Inventors: Werner Krause; Herbert Schumann, both of Berlin, Germany

[73] Assignee: Schering Aktiengesellschaft, Berlin, Germany

[21] Appl. No.: 09/242,673

[22] PCT Filed: Aug. 18, 1997

[86] PCT No.: PCT/DE97/01823

§ 371 Date: May 7, 1999

§ 102(e) Date: May 7, 1999

[87] PCT Pub. No.: WO98/07732

PCT Pub. Date: Feb. 26, 1998

[30] Foreign Application Priority Data

Aug. 23, 1996 [DE] Germany .............. 196 35 419

[51] Int. Cl.$^7$ .......................... C08G 79/00; A61K 49/04

[52] U.S. Cl. ............................. 528/395; 534/10; 556/64; 424/9.4; 424/1.11; 424/1.65; 424/9.1; 424/9.3; 424/9.411; 424/9.5

[58] Field of Search .................... 424/9.4, 1.11, 424/1.65, 9.1, 9.3, 9.411, 9.5; 534/10; 556/64; 528/395

[56] References Cited

FOREIGN PATENT DOCUMENTS

| | | |
|---|---|---|
| 2125188 | 6/1993 | Canada . |
| 716091 | 6/1996 | European Pat. Off. . |
| 9310824 | 6/1993 | WIPO . |
| 9622994 | 8/1996 | WIPO . |

*Primary Examiner*—Duc Truong
*Attorney, Agent, or Firm*—Millen, White, Zelano, & Branigan, P.C.

[57] ABSTRACT

The invention relates to dendrimeric organometallic bismuth compounds (bismuth dendrimers), which can advantageously be used as x-ray contrast media, as well as processes for their production.

14 Claims, No Drawings

BISMUTH DENDRIMERS, PROCESSES FOR THEIR PREPARATION, AND THEIR USE AS X-RAY CONTRAST AGENTS

The invention relates to dendrimeric organometallic bismuth compounds (bismuth dendrimers), which can advantageously be used as x-ray contrast media, as well as processes for their production.

PRIOR ART

The contrast media that are currently commonly used in diagnostic radiology contain either barium or iodine as an opacifying element. All of the contrast media that can be administered parenterally and that are currently approved contain iodine, either with three or with six iodine atoms per molecule (D. P. Swanson, H. M. Chilton, J. H. Thrall, "Pharmaceuticals in Medical Imaging," 1990, McMillan). In these compounds, the iodine atoms are always covalently coupled to the "carrier molecule," and they make possible the visualization of those vessels, organs and tissues that are achieved by the iodine-containing contrast media. The presence of the contrast medium increases the x-ray opacity of these tissues relative to their surrounding area in such a way that they are visible in the x-ray image and allow diagnoses relative to their shape or pathological changes. With these contrast media, a number of different diagnostic processes can be used, such as, e.g., for the water-soluble, iodine-containing compounds: angiography, urography, myelography and cholecystography.

Barium is used exclusively for the visualization of the gastrointestinal tract in the form of non-water-soluble barium sulfate as a formulation that is to be administered orally.

In the past, however, a number of novel types of contrast media were also proposed or studied that in a large number of cases represent metal complexes (e.g., R. M. Nalbandian, W. T. Rice, W. O. Nickels, Annals of N.Y. Acad. Sc., 1959, 79, 779–792; WO 90/03804; U.S. Pat. No. 4,310,507, U.S. Pat. No. 4,478,816, U.S. Pat. No. 4,647,447, U.S. Pat. No. 4,176,173, U.S. Pat. No. 5,417,958). The goal in the search for contrast media without iodine lies in avoiding the known side effects of the iodine-containing compounds such as pseudoallergic reactions, chemotoxic effects as well as the side effects of iodide that is released to the thyroid. The drawback of metal complexes lies in the usually relatively low metal content or the overly low solubility of the metal complexes, which is generally too low for use as x-ray contrast media.

Bismuth-organic compounds, which can sometimes also be used as x-ray contrast media, have been described in, e.g., EP 0 716 091 A1, JP A 4-154622, Vestn. Leningrad Univ., Fisz., Khim. Vol. 4, pp. 113–116 (1976), J. Chem. Soc., Chem. Commun., Vol. 16, pp. 1143–4 (1992), J. Coord. Chem., Vol. 12, pp. 53–57 (1982). Bismuth dendrimers have not yet been described, however.

The object of this invention now consists in designing contrast media for use in diagnostic radiology that do not contain any iodine and thus cannot cause the side effects that are induced by this element. It has now been found, surprisingly enough, that novel bismuth-organic compounds that have not yet become known, so-called bismuth dendrimers, can be used as x-ray contrast media.

The structure of these new compounds corresponds to general formula I

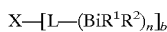  (I)

whereby

X stands as a central unit for O, S, N, P, C, Si, Sn, Ge, Bi, or for an aryl, heteroaryl, alkyl or cycloalkyl group, which can contain heteroatoms and/or alkyl, hydroxy, polyhydroxyalkyl substituents and/or ester, amide, thioester, thioamide, acetal, ketal, thioacetal, thioketal, disulfide, anhydride and/or urea groups, whereby X has base multiplicity b, L stands for a $C_1$–$C_{10}$ alkylene group, which can be hydroxy-substituted in zero to ten places, and can contain zero to ten aryl or heteroaryl, ether, ester, thioether, thioester, amide, thioamide, sulfonate, sulfonamide, phosphonate or phosphoric acid amid groups, n is 1 to 10, preferably 1 to 5, $R^1$, $R^2$, independently of one another, stand for another unit of formula Ia

  (Ia)

or $R^1$, $R^2$, independently of one another, stand for a branched or unbranched $C_6$–$C_{10}$ aryl or benzyl group that is hydroxy-substituted in zero to six places, an ether group —$OR^3$, ester group —$COOR^3$, thioether group —$SR^3$, thioester group —$COSR^3$, amide group —$CONR^3R^4$ or thioamide group —$CSNR^3R^4$, in which $R^3$, independently of one another, stand for a branched or unbranched $C_1$–$C_6$ alkyl group that is hydroxy-substituted in zero to six places, a $C_6$–$C_{10}$ aryl or benzyl group that is hydroxy-substituted in zero to six places, $R^4$, independently of one another, stand for a hydrogen atom or a branched or unbranched $C_6$–$C_{10}$ aryl or benzyl group that is hydroxy-substituted in zero to six places.

The invention therefore relates to bismuth-organic compounds of general formula I, as they are identified by the claims.

The term dendrimer was defined by Tomalia (D. A. Tomalia, Spektrum der Wissenschaft [Spectrum of Science], September 1995, pages 42–47). Understood by it is a polymer compound, in which a central molecule ("initiator core") is surrounded concentrically by monomer layers. A characteristic feature of dendrimers is an increasing number of branches from the inside toward the outside.

In the compounds according to the invention, the branches are produced by bismuth atoms. The bismuth-containing monomer formulations that are applied in succession are also referred to as generations in this document.

As central unit X, a central atom such as O, S, N, P, C, Si, Sn, Ge or Bi, or an aryl, heteroaryl, alkyl or cycloalkyl group, which can contain heteroatoms and/or alkyl, hydroxy or polyhydroxyalkyl substituents, is used in the compounds according to the invention. Central unit X can also be referred to as the zeroth generation.

Central unit X, however, can also contain a metabolically cleavable bridge, such as, for example, an ester, amide, thioester, thioamide, acetal, ketal, thioacetal, thioketal, disulfide, anhydride or urea bond, in such a way that the bismuth dendrimer according to the invention can be degraded in the human or animal organism.

A bismuth atom is preferably used as a central unit of the dendrimer.

Variable b stands for the base multiplicity of the central unit, i.e., for the number of reactive positions of the central unit, which can be linked with the first generation of bismuth-containing monomers. Base multiplicity b of oxygen and sulfur is, for example, 2, of bismuth, nitrogen and phosphorus 3, of silicon, germanium and tin 4. If the central unit of the organic groups is formed, the base multiplicity can lie between 1 and 12.

Group L is a connecting link between two generations. Starting from the central unit (zeroth generation), the first generation of bismuth-containing organyls is connected via a group L.

Group L can also contain a metabolically cleavable bridge, such as, for example an ester, amide, thioester, thioamide, acetal, ketal, thioacetal, thioketal, disulfide, anhydride or urea bond, in such a way that the bismuth dendrimer according to the invention can be degraded in the human or animal organism.

Connecting link L can also be a $C_6$–$C_{10}$ alkylene group. This group can be hydroxy-substituted in zero to ten places. It can also contain zero to ten aryl or heteroaryl, ether, ester, thioether, thioester, amide, thioamide, sulfonate, sulfonamide, phosphonate or phosphoric acid amide groups.

L preferably stands for an ethylene or a propylene group.

Groups $R^1$ and $R^2$ can stand either for another generation of bismuth-containing monomers of formula Ia $$L\text{—}BiR^1R^2 \qquad (Ia)$$

or in the last generation for an organic group, such as, e.g.:
 a branched or unbranched $C_{1-6}$ alkyl group that is hydroxy-substituted in zero to six places, or
 a $C_6$–$C_{10}$ aryl or benzyl group that is hydroxy-substituted in zero to six places,
 an ether group —$OR^3$,
 an ester group —$COOR^3$,
 a thioether group —$SR^3$,
 a thioester group —$COSR^3$,
 an amide group —$CONR^3R^4$
 a thioamide group —$CSNR^3R^4$.

Groups $R^3$ that are optionally contained in groups $R^1$ and $R^2$ stand for branched or unbranched $C_1$–$C_6$ alkyl groups that are hydroxy-substituted in zero to six places or for $C_6$–$C_{10}$ aryl or benzyl groups that are hydroxy-substituted in zero to six places.

Groups $R^4$ that are optionally contained in groups $R^1$ and $R^2$ stand for hydrogen atoms or for branched or unbranched $C_1$–$C_6$ alkyl groups that are hydroxy-substituted in zero to six places, or for $C_6$–$C_{10}$ aryl or benzyl groups that are hydroxy-substituted in zero to six places.

For the compounds according to the invention, it holds true that groups L, $R^1$ and $R^2$ can be different in each generation.

The compounds that contain hydrophilic groups, such as hydroxy, carboxy, amido, ether, thioether, ester or thioester groups, are preferred.

Owing to the symmetry of the molecule, the hydrophilic dendrimers according to the invention generally contain at least as many hydrophilic groups as there are bismuth atoms of the last generation. A dendrimer of base multiplicity 3 (b=3) with one generation (n=1) carries, for example, 3 bismuth atoms in the last generation and generally thus contains at least 3 hydrophilic groups. If the bismuth atoms of the last generation carry several hydrophilic groups, the number of hydrophilic groups of the entire molecule is a multiple of it. A dendrimer of base multiplicity 3 (b=3) with one generation (n=1) can thus contain 6 hydrophilic groups. The invention preferably relates to those dendrimers in which all groups $R^{1R}1$ and $R^2$ of the last generation contain hydrophilic substituents.

Groups $R^1$ and $R^2$ in the last generation preferably stand for a branched or unbranched $C_1$–$C_6$ alkyl group that is hydroxy-substituted in zero to six places, especially preferably for the 2,3-dihydroxypropyl radical.

Examples of compounds with bismuth as a central unit of base multiplicity three and one or two generations are depicted below:

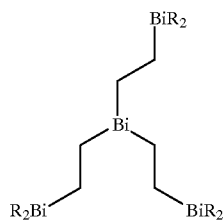

For R=—$CH_2CONHCH_2(CHOH)CH_2OH$, the summation formula is $Bi_4C_{36}H_{72}N_6O_{18}$. The molecular weight is 1712, and the relative bismuth content of the molecule is approximately 49%. The molecule is nonionic.

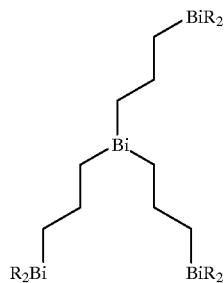

For R=—$CH_2CONHCH(CH_2OH)_2$, the summation formula is $Bi_4C_{39}H_{78}N_6O_{18}$. The molecular weight is 1754, and the relative bismuth content of the molecule is approximately 48%. The molecule is nonionic.

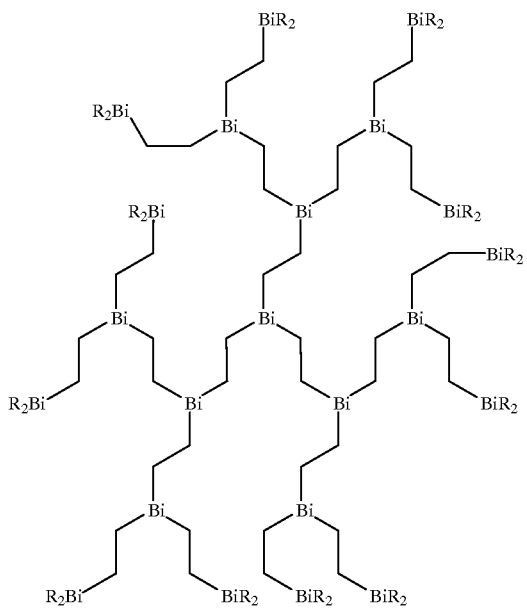

For R=—$CH_2CONHCH_2(CHOH)CH_2OH$, the summation formula is $Bi_{22}C_{100}H_{200}N_{12}O_{36}$. The molecular weight is 6742, and the relative bismuth content of the molecule is approximately 68%. The molecule is nonionic.

Methods for the production of these compounds are familiar to one skilled in the art. By way of example, but not limited to these processes, the following method can be mentioned.

Production Method

Step-by-step (consecutive) reaction of bismuth halides with organometallic compounds, e.g., Grignard compounds, characterized in that compounds of general formula II $$XHal_b \qquad (II)$$

are reacted with organometallic compounds of general formula III $$MHal(Y-CH=CH_2)_m \qquad (III)$$

whereby

X represents a central unit,

Hal represents a halogen atom,

M represents a metal atom, e.g., Mg, b corresponds to the base multiplicity of the central unit, m corresponds to the charge number of M that is reduced by 1, Y is a direct bond or a group L, whereby L stands for a $C_1$–$C_{10}$ alkylene group, which can be hydroxy-substituted in zero to ten places and can contain zero to ten aryl or heteroaryl, ether, ester, thioether, thioester, amide, thioamide, sulfonate, sulfonamide, phosphonate or phosphoric acid amide groups.

The compounds of general formula IV $$X(Y-CH=CH_2)_b \qquad (IV)$$

that are obtained can then be reacted with, e.g., HHal to compounds of general formula V $$X(Y-CH_2-CH_2Hal)_b \qquad (V)$$

From the above are produced the corresponding organometallic compounds of general formula VI $$X(Y-CH_2-CH_2MHal)_b \qquad (VI)$$

which are reacted either with compounds of general formula VII $$BiHal_3 \qquad (VII)$$

or—in the last dendrimer generation—with compounds of general formula VIII $$BiHalR^1R^2 \qquad (VIII)$$

whereby $R^1$, $R^2$, independently of one another, stand for a branched or unbranched $C_6$–$C_{10}$ aryl or benzyl group that is hydroxy-substituted in zero to six places, an ether group —$OR^3$, ester group —$COOR^3$, thioether group —$SR^3$, thioester group —$COSR^3$, amide group —$CONR^3R^4$ or thioamide group —$CSNR^3R^4$, in which $R^3$, independently of one another, stand for a branched or unbranched $C_1$–$C_6$ alkyl group that is hydroxy-substituted in zero to six places, a $C_6$–$C_{10}$ aryl or benzyl group that is hydroxy-substituted in zero to six places, $R^4$, independently of one another, stand for a hydrogen atom or a branched or unbranched $C_6$–$C_{10}$ aryl or benzyl group that is hydroxy-substituted in zero to six places.

The new compounds meet the requirements for contrast media, especially for x-ray contrast media. They are especially suitable for computer tomography.

The compounds according to the invention with molecular weights of up to about 10,000 are especially suitable for the visualization of the extracellular space.

The compounds according to the invention with molecular weights that are greater than 10,000 are suitable for the visualization of the intravascular space.

The compounds according to the invention are also suitable for the visualization of tumors, infarcted tissue or inflammations.

The compounds according to the invention can also be used as contrast media in MRI-, ultrasound- and radiodiagnosis. Moreover, they are used in therapy.

What is claimed is:

1. Dendrimeric compounds of general formula I $$X-[L-(BiR^1R^2)_n]_b \qquad (I)$$

whereby

X stands as a central unit for O, S, N, P, C, Si, Sn, Ge, Bi, or for an aryl, heteroaryl, alkyl or cycloalkyl group, which can contain heteroatoms and/or alkyl, hydroxy, polyhydroxyalkyl substituents and/or ester, amide, thioester, thioamide, acetal, ketal, thioacetal, thioketal, disulfide, anhydride and/or urea groups, whereby X has base multiplicity b, L independently of one another, stand for a $C_1$–$C_{10}$ alkylene group, which can be hydroxy-substituted in zero to ten places, and can contain zero to ten aryl or heteroaryl, disulfide, anhydride, thioketal, thioacetal, ketal, ether, ester, thioether, thioester, amide, thioamide, urea, sulfonate, sulfonamide, phosphonate or phosphoric acid amid groups, n is 1 to 10, b is the base multiplicity of the central unit, $R^1$, $R^2$, independently of one another, stand for another unit of formula Ia $$L-BiR^1R^2 \qquad (Ia)$$

or $R^1$, $R^2$, independently of one another, stand for a branched or unbranched $C_6$–$C_{10}$ aryl or benzyl group that is hydroxy-substituted in zero to six places, an ether group —$OR^3$, ester group —$COOR^3$, thioether group —$SR^3$, thioester group —$COSR^3$, amide group —$CONR^3R^4$ or thioamide group —$CSNR^3R^4$, in which $R^3$, independently of one another, stand for a branched or unbranched $C_1$–$C_6$ alkyl group that is hydroxy-substituted in zero to six places, a $C_6$–$C_{10}$ aryl or benzyl group that is hydroxy-substituted in zero to six places, $R^4$, independently of one another, stand for a hydrogen atom or a branched or unbranched $C_6$–$C_{10}$ aryl or benzyl group that is hydroxy-substituted in zero to six places.

2. Dendrimeric compounds according to claim 1, characterized in that n is a natural number from 1 to 5.

3. Compounds according to claim 1, wherein a bismuth atom forms central unit X.

4. Compounds according to claim 1, wherein L stands for an ethylene or propylene group in at least one generation.

5. Compounds according to claim 1, wherein they have two or three generations.

6. Compounds according to claim 1, wherein groups $R^1$ and $R^2$ in the last generation stand for a 2,3-dihydroxypropyl radical.

7. Compounds according to claim 1, further incorportated into diagnostic agents and/or therapeutic agents.

8. Compounds according to claim 1, further incorportated into contrast media for x-ray, MRI, ultrasound or radiodiagnostic technology.

9. Compounds according to claim 1, further incorporated into contrast media for computer tomography.

10. Compounds according to claim 1, further incorporated into contrast media for the visualization of the extracellular space or the intravascular space.

11. Compounds according to claim 1, which have molecular weights greater than 10,000.

12. Compounds according to claim 1, which have molecular weights of up to 10,000.

13. In a method of visualizing tumors, infected tissue or inflamation within a patient, wherein the improvement comprises administering a compound according to claim 1.

14. In a method of visualizing extracellular space within a patient, wherein the improvement comprises administering a compound according to claim 12.

* * * * *